US012702597B2

(12) United States Patent
Koplin et al.

(10) Patent No.: US 12,702,597 B2
(45) Date of Patent: Aug. 11, 2026

(54) DIGITALLY PRINTED BACKSHEET FILM

(71) Applicant: RKW SE, Mannheim (DE)

(72) Inventors: Robert Koplin, Dittenheim (DE); Christoph Meier, Dittenheim (DE); Dennis Becker, Ansbach (DE)

(73) Assignee: RKW SE, Mannheim (DE)

( * ) Notice: Subject to any disclaimer, the term of this patent is extended or adjusted under 35 U.S.C. 154(b) by 361 days.

(21) Appl. No.: 18/275,658

(22) PCT Filed: Dec. 21, 2021

(86) PCT No.: PCT/EP2021/086997
§ 371 (c)(1),
(2) Date: Aug. 3, 2023

(87) PCT Pub. No.: WO2022/167140
PCT Pub. Date: Aug. 11, 2022

(65) Prior Publication Data

US 2024/0099910 A1 Mar. 28, 2024

(30) Foreign Application Priority Data

Feb. 4, 2021 (DE) ........................ 102021102610.5

(51) Int. Cl.
*A61F 13/514* (2006.01)
*C09J 11/04* (2006.01)
*C09J 123/08* (2006.01)

(52) U.S. Cl.
CPC ......... *A61F 13/51458* (2013.01); *C09J 11/04* (2013.01); *C09J 123/0853* (2013.01); *A61F 2013/5147* (2013.01)

(58) Field of Classification Search
CPC ........ A61F 13/51458; A61F 2013/5147; A61F 13/51496; C09J 11/04; C09J 123/0853; C08K 2003/2206; A61L 15/18; A61L 15/42; A61L 15/585; C08L 23/06; C08L 23/0853; C08J 5/18; C08J 2323/00
See application file for complete search history.

(56) References Cited

U.S. PATENT DOCUMENTS 6,015,764 A * 1/2000 McCormack ........... B32B 27/20 442/373
2003/0235681 A1* 12/2003 Sebastian ............. G03G 7/0013 428/195.1
2004/0146729 A1* 7/2004 Ahmed ................... B32B 27/32 428/500
2005/0054780 A1* 3/2005 Zhou ...................... C09J 123/10 525/240
2005/0176331 A1* 8/2005 Martin .............. A61F 13/51458 442/327
2005/0176872 A1* 8/2005 Martin ....................... C09J 5/02 524/515
2006/0003150 A1* 1/2006 Braverman .......... B41M 5/0011 428/195.1
2006/0251858 A1* 11/2006 Thomas ............ A61F 13/51464 428/138
2010/0273380 A1* 10/2010 Chen ....................... B32B 27/12 428/221
2011/0091714 A1* 4/2011 Chen .......................... C08J 5/18 427/245
2011/0092869 A1* 4/2011 Chen ....................... B32B 27/30 128/849
2013/0189503 A1* 7/2013 Kozee ........................ B41J 2/01 347/20
2014/0005620 A1* 1/2014 Wang ...................... B29C 48/49 428/220
2014/0018759 A1* 1/2014 Jayasinghe ....... A61F 13/51464 604/370
2015/0175792 A1* 6/2015 Chou ................. C08L 23/0869 525/379
2017/0129228 A1* 5/2017 Middlesworth ......... B29C 55/18
2017/0152377 A1* 6/2017 Wang ......................... C08J 5/00
2017/0333264 A1 11/2017 Chatterjee et al.
2018/0141304 A1* 5/2018 Franklin .................. B29D 7/01
2019/0060507 A1* 2/2019 Tang ..................... A61F 13/514
2021/0237418 A1* 8/2021 Börmann .............. B32B 27/302
2021/0370650 A1* 12/2021 Campos Beceiro ...... B32B 7/12

FOREIGN PATENT DOCUMENTS

| | | |
|---|---|---|
| JP | 6767021 | 9/2020 |
| WO | 9829480 | 7/1998 |
| WO | 2019206769 | 10/2019 |
| WO | 2020225165 | 11/2020 |

* cited by examiner

*Primary Examiner* — Jeffrey M Wollschlager
(74) *Attorney, Agent, or Firm* — Volpe Koenig

(57) ABSTRACT

A breathable, polyolefinic, filled, stretched film. The film has a water vapor transmission rate of at least 500 g/m$^2$ in 24 h according to ASTM D6701-01. The water column of the film is more than 300 mm according to EDANA WSP 80.6. The film has an imprint which is bonded to the film via an adhesive. The film has at least one layer in which the adhesive is integrated.

12 Claims, No Drawings

DIGITALLY PRINTED BACKSHEET FILM

CROSS-REFERENCE TO RELATED APPLICATIONS

This application is a 371 national phase of PCT/EP2021/086997, filed Dec. 21, 2021, which claims priority from German Patent Application No. 10 2021 102 610.5, filed Feb. 4, 2021, both of which are incorporated herein by reference as if fully set forth.

TECHNICAL FIELD

The invention relates to a breathable, polyolefinic, filled, stretched film comprising an imprint which is bonded to the film via an adhesive, to a method for producing same, and to the use thereof.

BACKGROUND

In the case of disposable diapers, the outer side is formed from a liquid-impermeable film, often in combination with a nonwoven fabric, which prevents excretions from escaping. The film forms a layer which is arranged facing away from the carrier and is referred to as the "backsheet". While gas-impermeable plastics films were initially used, breathable, polyolefinic films have now been in use for quite some time.

Polyolefins are polymers prepared from alkenes such as ethylene and propylene by chain polymerization. They are semicrystalline thermoplastics that are easy to process.

The film according to the invention is a filled film, where breathability is achieved by adding hard fillers to the polymer matrix prior to extrusion and by stretching the extruded film. These films, which are impermeable to liquids but at the same time permeable to water vapor, significantly improve the wearing comfort of the diaper, since the breathability allows the diapers to self-dry and thus avoids skin irritation. In addition, the breathability counteracts diaper dermatitis. By removing moisture, a more skin-friendly climate is created in the diaper, so that skin irritation is significantly reduced.

A film which includes all of these above-described properties is described in WO 2020/225165 A1.

The backsheet film is printed to identify the diaper brand and to configure the optical impression of the diaper.

One frequently used process for printing the diaper film is flexographic printing. This is a direct letterpress process which is also referred to as a web-fed rotary printing process. The flexible printing plates, consisting of photopolymer or rubber, are used in combination with low-viscosity printing inks. The raised areas of the printing forme carry the image. The advantages reside in the economy through the exploitation of a large printing width and a high printing speed, and also the availability of inexpensive printing inks. The printing tools, photopolymer printing plates and/or laser-engraved elastomer sleeves are readily available. Large runs can be produced economically with flexographic printing. The disadvantages are the costs and the time required for the print-technological development of the motifs, the production and shipping of the motifs, and for setting up the tool in the flexographic printing system. As a result, this process is only economical for large print runs. In addition, the repeat length is limited, that is to say the print image including the distance to the next print image, which means that only three to four print designs can be printed, taking into account the average diaper dimensions. This limits the range of variations.

Digital printing is suitable for increasing the range of variations while at the same time making small print series economical. The term encompasses a group of printing processes in which the print image is transmitted to a printing machine as digital data. Laser printing and inkjet printing are the most common. The great advantage of digital printing consists in that it does not require a static, unchanging printing forme. Instead, pixel addressing within the print format is generated dynamically for each individual print operation, meaning that each print copy can have a different print image if required.

In digital printing, the printability of a medium depends on its surface properties and on the type of ink used. It is crucial for a successful print image that the printing ink forms as optimal as possible a bond with the surface of the material to be printed. It often proves to be advantageous for the ink to adhere to the surface such that it is neither repelled nor completely absorbed.

The commercially available, predominantly polar printing inks for digital printing adhere poorly, in particular to backsheet films. Backsheet films are special, breathable polyolefin films that have a hydrophobic and non-polar surface. For printing polyolefin films, an adhesion promoter is usually applied to the film, for example using a printing tool, to which the digital printing ink adheres well. Adhesion promoters have the disadvantage that they seal the pores of the backsheet film, which means that a significant part of the breathability can be lost.

WO 2019/206769 A1 describes a method for producing a printed nonwoven-film laminate, in which the printing ink contains an adhesion promoter or an adhesion promoter is applied with a printing device over the entire surface before printing. The adhesion promoter is, for example, an ethylene-vinyl acetate copolymer (EVA).

SUMMARY

The object of the invention is to provide a film which has the lowest possible specific weight per unit area and can be flexibly printed. Furthermore, the film should be suitable for the application of a multitude of different print designs. The film is intended to be particularly breathable, liquid-tight and to have mechanical properties that are optimal for its use as backsheet, even in the printed state. Furthermore, the film is to be haptically pleasant for its application. The aim is to provide a maximally low-rustle film that possesses softness and suppleness. It is moreover intended to be suitable, inter alia, for lamination with a nonwoven. The film is intended to increase the quality of the diapers and satisfy the requirements of diaper production in modern processes.

According to the invention, this object is achieved by a breathable film, a method and a use having one or more of the features described herein. Preferred variants can be gathered from the claims, the description and the examples.

DETAILED DESCRIPTION

According to the invention, the film has at least one layer in which the adhesive is integrated. As a result, an imprint, preferably a digitally generated print layer, can be applied directly to the layer. This means that the application of an adhesion promoter layer can be dispensed with, with the result that the pores remain free and a high breathability of the film is ensured.

To produce the film, a composition according to the invention is extruded, preferably by means of blown film extrusion. A microporosity is then created in a downstream stretching process. The combination of the extrusion with the stretching process and the composition according to the invention forms a hitherto unknown adhesive structure in at least one layer of the film.

The embedding according to the invention of an adhesive as a structure into the polymer matrix of a film layer makes it possible to integrate a digital printing unit into the film production process. The stretching process is preferably followed by a digital printing unit, which applies the print image directly to the layer.

The adhesive structure integrated in the layer ensures that the print image is firmly bonded to the film and at the same time advantageously exhibits a high-contrast effect. No coalescence phenomena occur, as is otherwise the case with conventional films according to the prior art with polar printing inks on non-polar film layers.

In an advantageous variant of the invention, the imprint is designed as a print motif. In the field of disposable hygiene articles, the term print motif denotes the manufacturer-specific and thematic design part of an imprint.

The imprint can also be implemented as a colorless and/or white contrast layer or printing ink that does not cover the entire surface, on which a print image or print motif is then applied.

The inkjet printing inks to be used for the imprint are preferably printing inks with a low viscosity and are therefore almost as thin as water. In principle, aqueous, UV-curable and solvent-containing ink systems are suitable. These printing inks are specially adapted to the respective print heads and are therefore individually adapted to the respective printing machine.

The imprinting of the print motif is preferably conducted using a water-based and/or glycol-containing composition in which the suitable pigments are dispersed. Furthermore, the printing ink can also be of solvent-based configuration, for which a slow-drying solvent is best suited. The ink can moreover include binders and additives.

Hereinafter, reference is always made to digital printing with respect to the printing, with the alternative hitherto known printing methods being included therewith.

The film according to the invention moreover has a specific combination of features which is hitherto unknown for a digitally printable, polyolefinic film.

Surprisingly, the film according to the invention exhibits a high water vapor transmission rate despite the direct printing of the digitally generated print layer on the backsheet film according to the invention. The water vapor transmission rate is defined here according to ASTM D6701-01 and is more than 500 g/m$^2$ in 24 h.

At the same time, the printed film according to the invention has a high degree of tightness, meaning that an egress of liquid is reliably prevented. The film according to the invention has a water column of more than 300 mm, preferably more than 400 mm, in particular more than 500 mm. The method for measuring the water column is in accordance with EDANA WSP 80.6. The pressure increase is 10 mbar per minute. Distilled water is used as the test liquid. The test area is 100 cm 2 without supporting sieve.

The film layer to be printed is preferably hygroscopic. This hygroscopy describes the capacity for chemical binding with water.

It has proven to be particularly favorable if the chemical binding potential of the layer to be printed is more than 0.01 g of water, preferably more than 0.02 g of water, in particular more than 0.03 g of water and/or less than 0.06 g of water, preferably less than 0.05 g of water, in particular less than 0.04 g of water, based on a specific weight per unit area of 1 g/m$^2$ of the overall film.

The hygroscopicity of the layer to be printed enables the film to be printed directly without having to apply an additional adhesion promoter layer.

The stretching process configures the microporosity of the film, as a result of which special hygroscopic materials that are integrated in the layer to be printed become accessible via the micropores. The printing inks for digital printing are usually pigments dissolved in polar solvent. After the printing ink has been applied, the pigments adhere to the layer, while the hygroscopic fillers chemically bind at least a portion of the polar solvent. This ensures an optimal print image, especially for digital printing processes.

According to the invention, the adhesive structure integrated into the layer increases the surface tension of the breathable film compared to known polyolefinic films, as a result of which the print layer adheres directly to the film according to the invention without the application of an adhesion promoter layer.

In a particularly advantageous variant of the invention, the adhesive includes an ethylene-vinyl acetate copolymer (EVA). The proportion of EVA in the layer is more than 5% by weight, preferably more than 10% by weight, in particular more than 15% by weight and/or less than 50% by weight, preferably less than 40% by weight, in particular less than 30% by weight.

Advantageously, the EVA has a vinyl acetate proportion of more than 10% by weight, preferably more than 15% by weight, in particular more than 20% by weight and/or less than 60% by weight, preferably less than 50% by weight, in particular less than 40% by weight. It has been found that the targeted embedding of EVA structures in a stretched polymer matrix forms particularly well-suited anchor points for color pigments of digital print layers.

In a variant of the layer according to the invention, the adhesive includes a polarizing additive, in particular, for example, a polar polyolefin wax. The polarizing additive also forms a structure integrated into the layer to be printed, this structure ensuring that the printing ink, in particular the color pigments, adheres directly to the layer. At the same time, polyolefin waxes excel preferably as added dispersing agent for better incorporation and integration of the additives in the masterbatch. Polyolefin waxes are transparent, colorless to white additions that produce clear melts and in the extruded state can be printed well.

For the application of the breathable, filled, stretched and directly digitally printed film according to the invention as a backsheet film for baby diapers, an abrasion-resistant adhesion of the printing ink is essential. Rubbed-off color particles on the baby's skin or on the clothing are undesirable and would cause lasting damage to the diaper manufacturer's image. The abrasion resistance of the print layer on the film can be evaluated using various test methods.

In the wet abrasion test, a drop of distilled water is allowed to act on various colored areas for 30 seconds. The surface is then rubbed ten times with a finger and the condition of the film is classified using the categories of high abrasion, satisfactory and low abrasion.

The Sutherland Rub Test is a test method in accordance with ASTM F 2497. A bond paper as abrading agent is loaded with a mass of four pounds and rubbed over the printed film for ten cycles. The printed layer is classified according to the categories good, satisfactory or poor.

In the ink tape test, a printed film has an adhesive tape stuck to it. The adhesive tape is pressed on four to six times with firm pressure. After a period of six to eight seconds, the adhesive tape is slowly pulled off from the film, which is attached to a solid substrate. The adhesive tape that has been pulled off is inspected for ink residues and classified into the categories of ink residue or no ink residue.

In the investigations, the film according to the invention exhibits good color stability and outstanding abrasion resistance. The film according to the invention can thus be used as a backsheet film for diapers without color erosion occurring when used as intended by customers.

The invention relates to a filled, breathable film. The film preferably has a high proportion of fillers, which serves to produce vacuoles in the stretching process, ensuring breathability.

Hard fillers are particularly suitable, with inorganic fillers preferably being used in the film according to the invention. The proportion of fillers is calculated such that stretching results not only in the formation of microporous pores but in addition in the presence of connections between the pores. Only a microporous film in which the pores are connected to one another has breathable properties as are required for backsheet applications.

The film according to the invention preferably has a proportion of fillers, in particular hard inorganic fillers, of more than 45% by weight, preferably more than 50% by weight, in particular more than 55% by weight. The solids content is preferably less than 75% by weight, in particular less than 70% by weight, preferably less than 65% by weight.

The filler content can be determined via known measuring methods such as ashing. A sample of known initial weight is heated to a temperature at which the polymer thermally decomposes but the filler does not. 560° C., for example, has proven to be of value for this purpose. The sample weight is then measured again. The polymer content per square meter can be calculated from the difference between the resulting weight and the initial weight.

As an alternative to ashing, a TGA measurement is possible, in which the weight of a sample is continuously measured during the heating. This test method can also clearly differentiate between polymer and filler and allows the polymer proportion of the film to be determined.

In a variant of the invention, calcium carbonate ($CaCO_3$) is used as filler, preferably with a mean particle size of 0.8 to 2 μm. During the stretching process, the elastic polymeric portions of the film are stretched and pores form at the edge of the chalk grains towards the polymer matrix. In a variant of the invention, the proportion of calcium carbonate is more than 45% by weight, preferably more than 50% by weight, in particular more than 55% by weight and/or less than 75% by weight, preferably less than 70% by weight, in particular less than 65% by weight.

In addition to or as an alternative to calcium carbonate ($CaCO_3$), a metal oxide component can be used as filler.

In a variant of the invention, metal oxide components are integrated into the polymer matrix in such a way that they can act as a filler to create breathability and/or as an adhesive for the imprint.

A dual function can be achieved by incorporating the metal oxide component into the composition of the masterbatch. In this way, both the outstanding breathability and the structure of the adhesive for adhesion of the print motif in the layer can be created at the same time.

Particularly advantageous metal oxide components are alkaline earth metal oxides, for ensuring, as filler, the formation of pores in the layer and/or at the same time, as adhesive, the adhesion of the print image. Calcium oxide (CaO) has proven to be particularly advantageous, although the use of magnesium oxide is also conceivable.

Thus, there are variants of the invention which almost exclusively contain calcium carbonate ($CaCO_3$) as filler, other variants which almost exclusively contain calcium oxide (CaO) as filler, and variants in which both substances are used in various ratios.

In a variant of the invention, the proportion of calcium oxide (CaO) in the layer to be printed is more than 20% by weight, preferably more than 30% by weight, in particular more than 40% by weight and/or less than 80% by weight, preferably less than 70% by weight, in particular less than 60% by weight.

In a particularly advantageous variant of the invention, CaO components are used, which act both as a filler and as an adhesive that is integrated as a structure in the layer to be printed, in order to enable optimal direct printing on the film.

These are preferably highly hygroscopic components that are suitable for binding a portion of the solvent of the printing ink that reaches the CaO particles via the microporous pores. Surprisingly, it has been found that these components bring about a particularly good binding of the solvent. As a result, the printing ink adheres well to the layer and thus facilitates a high production speed. These CaO components secondly form an adhesive structure integrated into the polymer matrix. As a result, polar printing inks adhere better to the film and prove to be particularly resistant to abrasion.

Preference is given to using CaO components having a mean particle size of less than 8 μm, preferably less than 5 μm, in particular less than 3 μm and/or than 0.5 μm, preferably less than 1.0 μm, in particular more than 1.5 μm.

In an advantageous variant of the film according to the invention, mixtures are used which contain both calcium carbonate components and calcium oxide components, with at least one or both components acting as a filler to create breathability and/or as an adhesive for the print.

In an alternative variant of the film according to the invention, the adhesive includes a silica component, the proportion of the silica component in the layer being more than 0.3% by weight, preferably more than 0.5% by weight, in particular more than 0.7% by weight and/or less than 20% by weight, preferably less than 15% by weight, in particular less than 10% by weight.

According to the invention, the breathable, polyolefinic, filled, stretched film has at least one layer. The thickness of the layer is preferably less than 6 μm, in particular less than 5 μm, preferably less than 4 μm and/or preferably more than 0.5 μm, in particular more than 1.5 μm, preferably more than 2.5 μm.

There is in principle the possibility of the film being configured as a monofilm. In a preferred variant of the invention, the film has at least one further layer, the thickness of this layer with preference being less than 14 μm, in particular less than 13 μm, preferably less than 12 μm and/or more than 6 μm, with preference more than 7 μm, in particular more than 8 μm.

Also conceivable are variants of the invention in which this further layer is disposed in the middle as a "support layer" and layers to be printed, having the features described above, are applied to both sides of this "support layer", so that a symmetrical "sandwich" arrangement is formed.

The film according to the invention with preference has a weight per unit area of less than 17 g/m$^2$, in particular less than 16 g/m$^2$, preferably less than 15 g/m$^2$ and/or with preference more than 10 g/m$^2$, in particular more than 11 g/m$^2$, preferably more than 12 g/m$^2$.

In advantageous variants of the invention, the films according to the invention have significantly better mechanical properties than conventional directly printable films. These properties are preferably ensured despite a low polymer content.

In a variant of the invention, the specific dart drop of the film is preferably more than 19 g per gram of polymer per square meter. In addition to these properties, the film preferably has an elongation at break in the machine direction of preferably less than 200%.

Moreover, the film according to the invention has a high water vapor transmission rate and nevertheless reliably ensures soakthrough protection.

Moreover, the two aforementioned properties are achieved with an elongation at break in the machine direction of preferably less than 250%. In a preferred embodiment of the invention, the elongation at break in the machine direction is even less than 170%, preferably less than 150%, in particular less than 130%.

The residual elongation at break in the machine direction serves as a parameter for the degree of stretching of the breathable film. The lower the residual elongation at break in the machine direction, the higher the degree of stretching of the breathable film. The elongation at break is defined according to ASTM D882. A test specimen of, for example, 25.4 mm (1 inch) is cut out and clamped in a suitable testing apparatus with a clamping length of 50.8 mm. A preliminary force of 0.05 newtons is applied, after which a tensile test is performed at a rate of 500 mm/min. The quotient of the final breaking of the film and the initial clamping length describes the elongation at break of the film, which is given as a percentage. Despite its high resilience, the film according to the invention has an exceptionally low elongation at break. This indicates pronounced stretching of the film in the machine direction. Pronounced stretching of the film in the machine direction results in a high stiffness of the film. For conventional films, pronounced stretching in the machine direction results in such a pronounced weakening in the cross direction that the conventional backsheet film is damaged when the diapers are folded in the converter or when the diapers are put on. In contrast to this, despite the pronounced stretching in the machine direction the film according to the invention proves to be extremely stable, even with respect to loads in the cross direction.

Due to the weakening of the film in the cross direction, conventional films typically cannot be subjected to such pronounced stretching, meaning that they generally have an elongation at break of more than 250% in the machine direction in order to ensure a minimum degree of mechanical stability in the cross direction. These conventional, relatively weakly stretched films have to be passed through the printing machine and the diaper converter at very low web tensions in order to be printed in a register-accurate manner and not to constrict too greatly in the machine direction during diaper production, since this would otherwise lead to leaks at the lateral edge of the diaper. In contrast, because the film according to the invention has been subjected to pronounced stretching and has only minor remaining residual elongation in the machine direction, it can be fed through the printing machine and diaper converter at high speeds. This results in extremely good printability of the film according to the invention.

With the film according to the invention, it has been possible for the first time to produce an extremely thin film with a low weight per unit area which, with low polymer use, is optimal for the production of breathable baby diapers and can be optimally printed even with modern digital printing machines at very high converter speeds.

This hitherto unknown direct printability of a polyolefinic film is achieved through a specific composition of the film, a targeted selection of polymers in combination with a specific production process.

Despite these astoundingly stable properties of the overall film, the polymer content of the film according to the invention is relatively low. The film preferably has a proportion of polymeric components of less than 60% by weight, preferably less than 50% by weight, in particular less than 45% by weight. However, in order to nevertheless ensure sufficient stability, the polymer proportion is more than 25% by weight, preferably more than 30% by weight, in particular more than 35% by weight.

In a particularly advantageous variant of the overall film according to the invention, the proportion of polyolefins in the polymer is more than 60% by weight, preferably more than 70% by weight, in particular more than 80% by weight.

In a variant of the invention, two different linear low-density polyethylene (LLDPE) components are used to produce the film according to the invention. An LLDPE component having a low density is combined with an LLDPE component having a high density.

The LLDPE component having a low density preferably has a density of less than 0.925 g/cm$^3$, in particular less than 0.920 g/cm$^3$. This LLDPE component is with preference used in a proportion of more than 5% by weight, in particular more than 20% by weight, preferably more than 30% by weight. The proportion of this component is less than 60% by weight, preferably less than 50% by weight, in particular less than 40% by weight.

This first LLDPE component having the low density is for example combined with a second LLDPE component with a higher density. The density of the second component is preferably more than 0.925 g/m$^3$, preferably more than 0.930 g/m$^3$. The proportion of this second LLDPE component having the higher density is with preference more than 2% by weight, preferably more than 4% by weight, in particular more than 5% by weight. Furthermore, the proportion of this second LLDPE component having the higher density is with preference less than 12% by weight, preferably less than 10% by weight, in particular less than 8% by weight.

Preferably, the first LLDPE component having the low density is an ethylene/1-hexene copolymer.

In a favorable embodiment of the invention, the film comprises a polypropylene component. The proportion of this polypropylene component is with preference more than 0.5% by weight, preferably more than 1% by weight, and in particular more than 2% by weight. The polypropylene component is present with preference in a proportion of less than 12% by weight, preferably less than 8% by weight, in particular 6% by weight.

In a variant of the invention, properties of the film are realized through the controlled use of blown film extrusion. At the same time, cast film extrusion is also conceivable. The blown film extrusion upstream of the stretching makes it possible to achieve the film properties according to the invention on the basis of the specific composition.

To create the microporosity, the film web is subjected to a stretching process. At least stretching in the machine direction (MD) is preferably effected here. In addition, stretching in the cross direction (CD) can also be effected. Ring rolling would also be possible in principle.

According to the invention, the film is with preference stretched by more than 200%, with preference in particular more than 280%, preferably more than 300%, in particular more than 320%. The stretching of the film after the blown film extrusion in the machine direction is, for example, less than 400%, preferably less than 365% and in particular less than 350%. A temperature of more than 70° C., preferably more than 80° C., in particular more than 90° C., is used with preference during the stretching. The temperature during the stretching in the machine direction is with preference less than 120° C., preferably less than 110° C., in particular less than 100° C.

According to the invention, the film is preferably used as a backsheet in a diaper.

Besides the breathable film itself, the invention also encompasses variants in which the film is for example combined with other materials, for example a nonwoven. The film according to the invention can be used either as a single backsheet or as a nonwoven-film laminate. The film can be bonded to a nonwoven fabric, for example by means of an adhesive. In addition, the nonwoven-film laminate can also be produced by a thermobonding process. The film and/or the nonwoven can be heated either over an area or at specific points by means of two heated rollers. For example, an embossing roller may be used with a smooth roller, for example a steel roller, as backing roller. The film and/or the nonwoven can be incipiently melted by high temperature and pressure. This bonds the film to the nonwoven. Moreover, nonwoven-film laminates may also be produced by means of thermolamination. In addition or as an alternative, nonwoven-film laminates may also be produced by means of ultrasonic lamination, for example using Herrmann Ultraschall technology.

The nonwoven-film laminates produced can be further processed in a known manner, with stretching in the machine direction and/or stretching in the cross direction or stretching in both directions also being possible. Single backsheets can also be further processed.

The invention also encompasses absorbent articles in which the film according to the invention is used. The absorbent article is preferably designed as a diaper, in particular as a baby diaper.

These absorbent articles generally have an absorbent core, an upper layer, and a lower layer. The film according to the invention is preferably used in the lower layer.

In the absorbent article according to the invention, the film according to the invention may be bonded to a nonwoven. Furthermore, the film or the film-nonwoven laminate can be provided with elastic ears, what are known as front or back ears. These can either be adhesively bonded to the film or else thermobonded. The absorbent core of the absorbent article preferably comprises a superabsorbent which is encased with a fabric.

The absorbent core can be provided with channels. In addition to the backsheet, the absorbent article also comprises a topsheet. The topsheet can be provided with a nonwoven. The topsheet can be bonded to the backsheet at least in regions. The topsheet may for example be laminated against the backsheet with a hot-melt adhesive.

The invention will be elucidated hereinbelow on the basis of examples, without the invention being restricted thereto.

The film according to the invention is preferably configured as a coex film. In this case, the film comprises at least one further layer in addition to the layer to be printed.

It is also possible for a layer to be printed to be disposed on either side of the further layer, in what is known as a sandwich arrangement.

The specifications for this further layer are the same for all examples. They are produced on the basis of a composition that is described in detail in WO 2020/225165 A1. Express reference is made here to these compositions without listing them again separately and without restriction thereto.

In the following examples only the layer to be printed is specified.

Example 1

The following components are used in example 1:

80% Granic WAC-GCR Group

20% EVA, Greenflex FL 65-Versalis

Granic WAC is an inorganic filler and adhesive in the form of calcium oxide mixed with a PE copolymer.

Greenflex FL65 is an EVA component with a VA content of 28% by weight. The density is 0.952 g/cm$^3$. The melt flow rate is 2.5 g/10 min (at 190° C. with 2.16 kg) according to ISO 1133.

The production process is similar for all films according to the examples and is described by way of example on the basis of this first example. To produce the film according to the invention, the polymer constituents are heated with the mineral fillers in an extruder, for example a compounding extruder, to a temperature well above the melting temperature of the polymer constituents (for example above 200° C.) and are melted together.

This is then followed according to the invention by blown film extrusion. A blown tube is formed in the blown film extrusion process. The tubular film formed is laid flat on top of one another and slit at the ends to form two film webs, each of which can be used as a starting film web. The inflation ratio is about 1:3.

The primary weight per unit area of the film is 46.2 g/m$^2$.

In the subsequent monoaxial stretching process, the film is stretched by a total of 330% in the machine direction. This total stretching factor results from the actual stretching in the machine direction by 350% at a roller temperature of 95° C. and subsequent heat treatment at a temperature of 106° C., with a shrinkback of 6% being allowed on the heat treatment rollers.

Example 2

The following components are used in example 2:

74% Granic WAC-GCR Group

20% EVA, Greenflex FL 65-Versalis

6% Polyplus AB-1064-LD

The Polyplus AB-1064-LD silica is an inorganic filler and adhesive in the form of silicon dioxide, preferably having an average particle size of 15 μm. A proportion of 15% silica is mixed with 85% LDPE carrier material.

Example 3

The following components are used in example 3:

74% Granic WAC-GCR Group

20% Exceed™ XP 8318 LLDPE from ExxonMobil

6% silica, Polyplast AB-1064-LD

The Exxon Exceed XP 8318 LLDPE is the first LLDPE component, having a lower density. Preferably, this LLDPE is metallocene catalyzed. It proves to be particularly favorable when an ethylene/1-hexene copolymer is used. This LLDPE has a density of 0.918 g/cm$^3$ according to ASTM D1505, a melt flow index of 1.0 g/10 min (at 190° C./2.16 kg) according to ASTM D1238 and a peak melting temperature of 121° C. according to the Exxon Mobil method.

Example 4

The following components are used in example 4:

47.72% calcium carbonate, Imerys Filmlink 400
30% EVA, Greenflex FL 65-Versalis
18.52% Dowlex™ SC2108 G LLDPE from DowDuPont
2.77% Dowlex™ 2006 HDPE from DowDuPont
1% additives (antioxidants and thermal stabilizer)

The filler used is an inorganic filler in the form of calcium carbonate, preferably having a particle size of 0.8 to 2 μm.

The Dowlex™ SC2108 G LLDPE is the second LLDPE component, having the higher density. The density is 0.935 g/cm$^3$. The melt flow rate is 2.6 g/10 min (at 190° C., 2.16 kg) according to ISO 1133.

The Dowlex™ 2006 HDPE has a density of 0.961 g/cm$^3$ according to ASTM D1505, a melt flow index of 8.0 g/10 min (at 190° C./2.16 kg) according to ASTM D1238.

Example 5

The following components are used in example 5:

80% Granic WAC-GCR Group
20% Exceed™ XP 8318 LLDPE from ExxonMobil

Example 6

The following components are used in example 6:

25.08% calcium carbonate, Imerys Filmlink 400
40% Granic WAC-GCR Group
25% Exceed™ XP 8318 LLDPE from ExxonMobil
6.1% Dowlex™ SC2108 G LLDPE from DowDuPont
3.2% Borpact™ BC918CF PP from *Borealis*
0.52% additives (antioxidants and thermal stabilizer)

Borpact™ BC918CF is a highly crystalline polypropylene having a density of 0.905 g/cm$^3$. The melt flow rate (at 230° C./2.16 kg) according to ISO 1133 is 3.0 g/10 min. The melting temperature (DSC) according to ISO 3146 is 166° C. The films according to the above examples have the following properties:

| | weight per unit area [g/m$^2$] | water vapor transmission rate [g/m$^2$/d] | MD tensile strength [N/cm] | MD elongation [%] | CD tensile strength [N/cm] | CD elongation [%] | water column [mm] |
|---|---|---|---|---|---|---|---|
| Example 1 | 14.1 | 5183 | 6.24 | 90 | 0.9 | 330 | 510 |
| Example 2 | 14.3 | 4510 | 7.28 | 97 | 0.93 | 332 | 490 |
| Example 3 | 14.3 | 5864 | 8.06 | 101 | 0.97 | 356 | 540 |
| Example 4 | 14.5 | 3978 | 8.23 | 122 | 1.12 | 403 | 500 |
| Example 5 | 13.7 | 5200 | 7.77 | 81 | 0.89 | 374 | 510 |
| Example 6 | 15.9 | 4820 | 9.48 | 60 | 0.95 | 409 | 520 |

The invention claimed is:

1. A breathable film, comprising:

a breathable, polyolefinic, filled, stretched film comprising more than 45% by weight fillers and an adhesive integrally formed therein, the film being formed by monaxial stretching as a layer and an imprint bonded thereon via the adhesive that is in the layer, the breathable film having a water vapor transmission rate of at least 500 g/m$^2$ in 24 h according to ASTM D6701-01; and a water column of more than 300 mm according to EDANA WSP 80.6, wherein the adhesive includes an ethylene-vinyl acetate copolymer (EVA), a proportion of EVA in the layer being more than 5% by weight and less than 50% by weight, and the EVA has a vinyl acetate proportion of more than 20% by weight and less than 60% by weight.

2. The breathable film as claimed in claim 1, wherein the imprint is disposed directly on the layer.

3. The breathable film as claimed in claim 1, wherein the imprint comprises a water-based or a glycol-containing composition.

4. The breathable film as claimed in claim 1, wherein the layer has a thickness of less than 6 μm and more than 0.5 μm.

5. The breathable film as claimed in claim 1, further comprising at least one further layer, a thickness of the at least one further layer being less than 14 μm and more than 6 μm.

6. The breathable film as claimed in claim 1, wherein the adhesive includes a metal oxide component, a proportion of the metal oxide component in the layer being more than 20% by weight and less than 80% by weight.

7. The breathable film as claimed in claim 6, wherein the adhesive includes calcium oxide, a proportion of the calcium oxide in the layer being more than 20% by weight and less than 80% by weight.

8. The breathable film as claimed in claim 1, wherein the layer has a thickness of less than 6 μm.

9. The breathable film as claimed in claim 1, further comprising at least one further layer, a thickness of the at least one further layer being less than 14 μm.

10. The breathable film as claimed in claim 6, wherein the metal oxide component comprises an alkaline earth metal oxide.

11. The breathable film as claimed in claim 1, wherein the adhesive includes a metal oxide component, a proportion of the metal oxide component in the layer being more than 20% by weight.

12. The breathable film as claimed in claim 6, wherein the adhesive includes calcium oxide, a proportion of the calcium oxide in the layer being more than 20% by weight.

* * * * *